(12) United States Patent  
Esser et al.

(10) Patent No.: US 12,053,259 B2  
(45) Date of Patent: Aug. 6, 2024

(54) SENSOR DEVICE HAVING A HOUSING WITH AT LEAST TWO CAVITIES

(71) Applicant: OSRAM OLED GmbH, Regensburg (DE)

(72) Inventors: Faina Esser, Regensburg (DE); Claus Jaeger, Regensburg (DE); Stephan Haslbeck, Regensburg (DE)

(73) Assignee: OSRAM OLED GmbH, Regensburg (DE)

( * ) Notice: Subject to any disclaimer, the term of this patent is extended or adjusted under 35 U.S.C. 154(b) by 965 days.

(21) Appl. No.: 16/980,150

(22) PCT Filed: Mar. 12, 2019

(86) PCT No.: PCT/EP2019/056189  
§ 371 (c)(1),  
(2) Date: Sep. 11, 2020

(87) PCT Pub. No.: WO2019/175193  
PCT Pub. Date: Sep. 19, 2019

(65) Prior Publication Data  
US 2021/0007604 A1 Jan. 14, 2021

(30) Foreign Application Priority Data  
Mar. 14, 2018 (DE) .......................... 102018105904.3

(51) Int. Cl.  
*A61B 5/00* (2006.01)  
*A61B 5/024* (2006.01)  
*A63B 24/00* (2006.01)

(52) U.S. Cl.  
CPC ........ *A61B 5/0059* (2013.01); *A61B 5/02427* (2013.01); *A61B 5/681* (2013.01);  
(Continued)

(58) Field of Classification Search  
CPC .................................................. A61B 5/0059  
See application file for complete search history.

(56) References Cited

U.S. PATENT DOCUMENTS 5,893,364 A 4/1999 Haar et al.  
9,763,584 B2 9/2017 Freschl et al.  
(Continued)

FOREIGN PATENT DOCUMENTS

CN 106551683 A 4/2017  
DE 102016105869 A1 10/2017  
WO 2017197033 A1 11/2017

*Primary Examiner* — Joel Lamprecht  
*Assistant Examiner* — Nyrobi Celestine  
(74) *Attorney, Agent, or Firm* — Slater Matsil, LLP

(57) ABSTRACT

In an embodiment a sensor device includes a housing having at least a first cavity and a second cavity, at least one light emitter arranged in the first cavity and at least one light detector arranged in the second cavity, wherein each of the cavities has an opening at an underside of the housing so that light from the respective cavity is passable to the outside and/or from the outside into the respective cavity, wherein each of the cavities includes a bottom opposite the underside of the housing and a peripheral side wall extending between the bottom and the underside of the housing, wherein at least one of the cavities is filled with an absorbing material from the bottom to a specified height, and with a transparent material from the specified height to a height of the underside of the housing, and wherein the light detector is arranged on the bottom of the second cavity.

19 Claims, 5 Drawing Sheets

(52) U.S. Cl.
CPC ...... *A63B 24/0062* (2013.01); *A61B 5/02416* (2013.01); *A61B 2560/0406* (2013.01); *A61B 2560/0462* (2013.01); *A61B 2562/0233* (2013.01); *A61B 2562/168* (2013.01); *A61B 2562/185* (2013.01)

(56) References Cited

U.S. PATENT DOCUMENTS

| | | |
|---|---|---|
| 2009/0326346 A1 | 12/2009 | Kracker et al. |
| 2010/0056887 A1 | 3/2010 | Kimura et al. |
| 2010/0258710 A1* | 10/2010 | Wiese ............... H01L 31/173 250/221 |
| 2012/0176599 A1* | 7/2012 | Leung ............... G01N 21/31 29/592.1 |
| 2014/0103199 A1* | 4/2014 | Loong ............... G01S 7/4813 250/214.1 |
| 2014/0276119 A1* | 9/2014 | Venkatraman ..... A61B 5/02405 600/509 |
| 2015/0282713 A1* | 10/2015 | Fei ............... A61B 5/02427 600/476 |
| 2016/0029911 A1* | 2/2016 | Lee ............... A61B 5/02427 600/407 |
| 2016/0061726 A1 | 3/2016 | Ness et al. |
| 2016/0198966 A1 | 7/2016 | Uematsu et al. |
| 2017/0086691 A1 | 3/2017 | Freschl et al. |
| 2017/0325698 A1* | 11/2017 | Allec ............... A61B 5/14552 |
| 2018/0182913 A1* | 6/2018 | Chen ............... G01S 7/4813 |
| 2018/0358501 A1* | 12/2018 | Huang ............... H01L 31/16 |

* cited by examiner

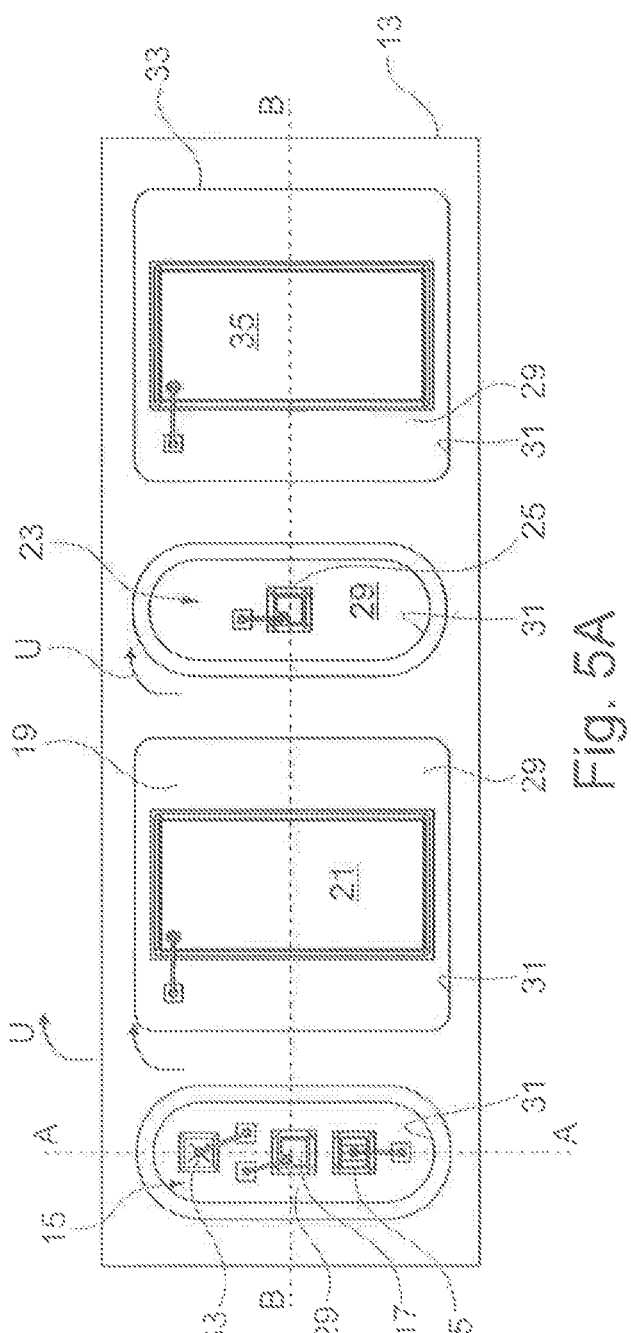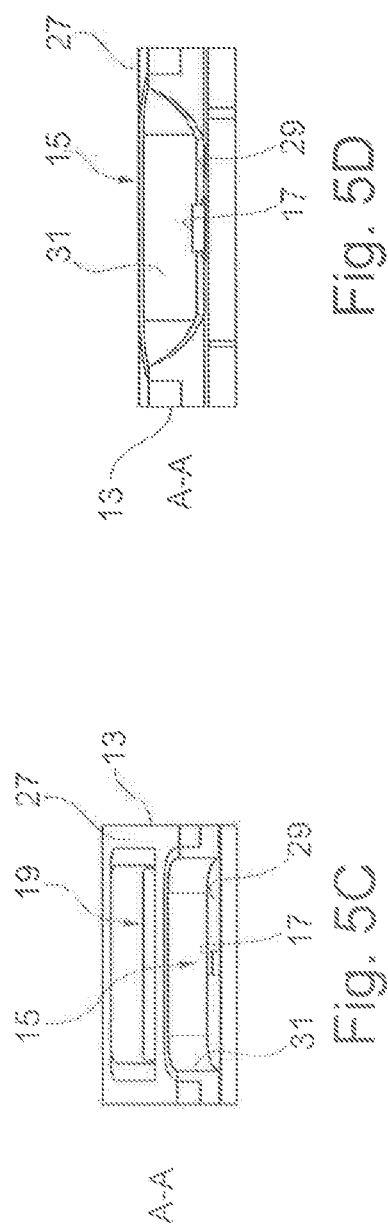

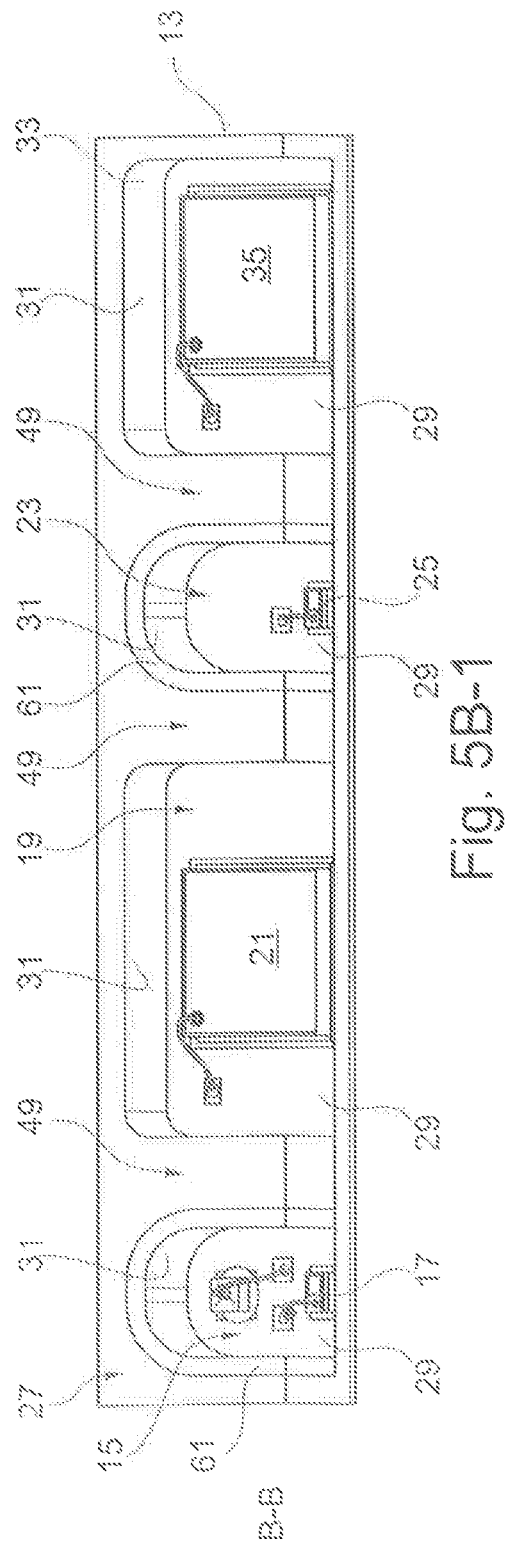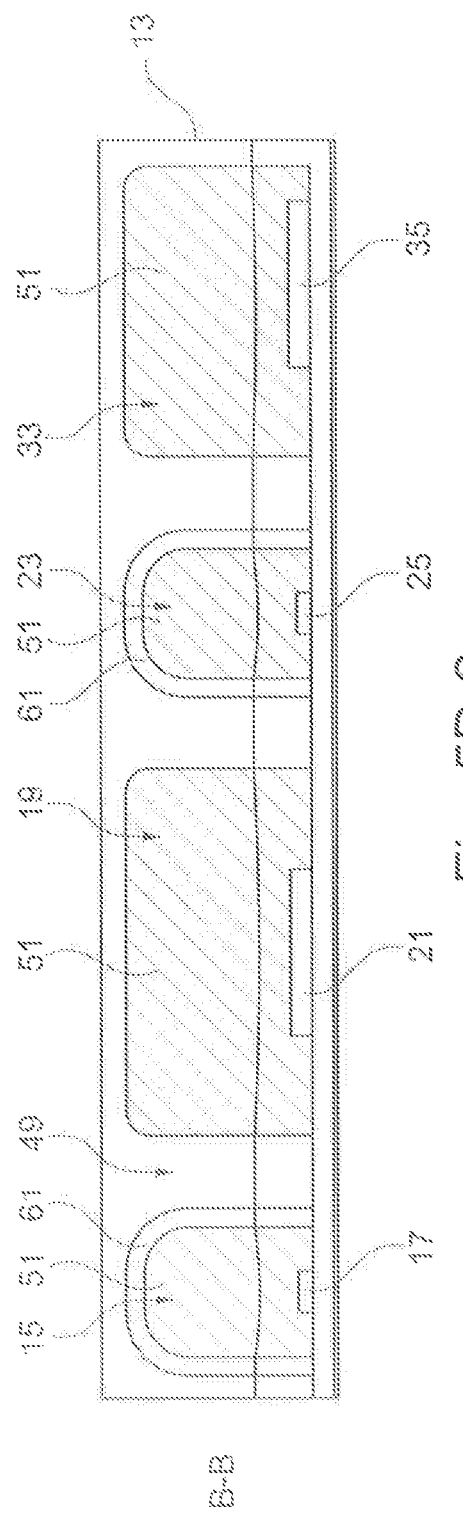

SENSOR DEVICE HAVING A HOUSING WITH AT LEAST TWO CAVITIES

This patent application is a national phase filing under section 371 of PCT/EP2019/056189, filed Mar. 12, 2019, which claims the priority of German patent application 102018105904.3, filed Mar. 14, 2018, each of which is incorporated herein by reference in its entirety.

TECHNICAL FIELD

The present invention relates to a sensor device.

BACKGROUND

A sensor device is known from German Application DE 10 2016 105 869 A1.

A sensor device of the type mentioned at the beginning can be used, for example, for optically measuring a heart rate. Used as a heart rate sensor, the sensor device is brought with its underside onto a suitable skin area of a test person, and light is irradiated into the upper skin layers of the test person by means of the light emitter, which may be a light-emitting diode, for example. There, the light is scattered, absorbed, and partially reflected as a function of the wavelength. The proportion of the reflected light varies due to the blood vessel volume varying with the heartbeat of the test person. This variation can be detected and evaluated by the light detector. However, the measured signal may be weak and superimposed by interferences.

In such sensor devices, improvement in signal quality is to be achieved and interferences are to be reduced.

SUMMARY

Embodiments provide a sensor device in which improved signal quality can be achieved and in which interferences in the detected signal are reduced.

Embodiments provide a sensor device of the type mentioned at the beginning in that, in the sensor device, the bottom and/or the side wall of the first cavity is designed differently in terms of color than the bottom and/or the side wall of the second cavity in order to achieve a higher reflectivity than the second cavity.

As a result of the different color design of the first cavity with the light emitter with respect to the second cavity with the detector, the reflectivity of the first cavity can be improved with respect to the reflectivity of the second cavity. It can thereby be achieved that a greater proportion of the light emitted by the light emitter can be coupled out of the first cavity, e.g., by multiple reflections at the bottom or at the side wall of the first cavity, and is thus available, for example, for measuring a vital function, such as the heart rate. The signal quality of the signal detected by the light detector or the signal-to-noise ratio of the signal can thus be improved.

In order to achieve a higher absorptance than the first cavity, the bottom and/or the side wall of the second cavity can be designed differently in terms of color than the bottom and/or the side wall of the first cavity. Light that enters the second cavity but does not pass directly to the detector can thereby be absorbed at the bottom and/or the side wall of the second cavity. Multiple reflections, which can lead to falsification of the measurement signal, can thus be avoided or reduced in the detector cavity. The signal quality of the signal detected by the light detector can thus be further improved, and interferences in the detected signal can be reduced.

The color of the bottom and/or of the side wall of the first cavity is preferably matched to the light emitted by the light emitter of the first cavity. The color of the bottom and/or of the side wall of the first cavity is preferably matched such that the bottom and/or the side wall has a reflectance of more than 50%, preferably more than 60%, more preferably more than 70%, even more preferably more than 80%, with orthogonally incident radiation for the wavelength range of the light emitted by the light emitter. High outcoupling of the light emitted by the light emitter from the first cavity can thereby be achieved.

The color of the bottom and/or of the side wall of the second cavity is preferably matched to the light emitted by the light emitter of the first cavity. The color of the bottom and/or of the side wall of the second cavity is preferably matched such that the bottom and/or the side wall has an absorptance of more than 50%, preferably more than 60%, more preferably more than 70%, even more preferably more than 80%, with orthogonally incident radiation for the wavelength range of the light emitted by the light emitter. As a result, the light impinging on the bottom and/or the side wall of the second cavity can be absorbed effectively, thereby preventing this light from passing to the detector, e.g., by means of multiple reflections.

The bottom and/or the side wall of the first cavity can be at least substantially white, in particular using titanium dioxide ($TiO_2$). High reflectivity of the bottom and/or of the side wall of the emitter cavity and thus good outcoupling of the light emitted by the light emitter from the first cavity can thereby be achieved. Titanium dioxide can be applied as a layer to the bottom and/or the side wall.

The bottom and/or the side wall of the second cavity preferably are at least substantially black. Impinging light can thus be absorbed effectively.

In the context of the present application, "black" and "white" are considered colors. A first cavity with a white bottom or a white side wall is thus regarded as being designed differently in terms of color than a second cavity with a black bottom or a black side wall.

The bottom and/or the side wall of the first cavity may comprise a metallic layer. The layer may in particular be a silver, aluminum, or gold layer. The bottom and/or the side wall may thus comprise a "metallic" color or a "metallic" color impression.

At least one of the cavities may be completely or partially filled with at least one, in particular transparent, casting compound. The casting compound preferably comprises a flat surface. This surface can lie in the same plane as the underside of the housing or in a plane parallel thereto. The casting compound can be formed, for example, from a resin or a silicone. As a result of a casting compound, in particular with a flat surface, the number of multiple reflections in the respective cavity is increased and, as a result of the use of a reflective, in particular white, material for the surfaces of the cavity, an improvement of the outcoupling efficiency in comparison to a black cavity can be achieved. A lens or another beam-shaping element may be arranged or formed on the surface of the casting compound.

A partition wall is preferably provided between the first cavity and the second cavity. As a result of the partition wall, an undesired so-called crosstalk between emitter and detector can be reduced or avoided.

The surface of the partition wall located on the underside of the housing may have a high absorptance. The absorptance is preferably more than 50%, preferably more than 60%, more preferably more than 70%, even more preferably more than 80%, with orthogonally incident radiation for the wavelength range of the light emitted by the light emitter. As a result, the light impinging on the surface of the partition wall can be absorbed effectively, thereby preventing this light from passing to the detector, e.g., by means of multiple reflections.

The surface of the partition wall may be at least substantially black. High absorptance can thereby be implemented in a simple manner.

In a preferred embodiment, the side wall of at least one of the cavities, in particular of the first cavity, may extend at least substantially orthogonally from the bottom of the cavity to the underside of the housing, at least over a section of the side wall extending in the peripheral direction. The side wall may thus comprise a straight profile orthogonal to the bottom.

According to a preferred embodiment, which is also claimed herein by means of an independent claim, the side wall of at least one of the cavities, in particular of the first cavity, comprises a curved profile from the bottom of the cavity to the underside of the housing, at least over a section of the side wall extending in the peripheral direction. The side wall may be designed in the manner of a reflector. The curved side wall makes it possible to achieve improved beam shaping and, associated therewith, improved light outcoupling from the cavity.

Optionally, the cavity may be filled with a casting compound, in particular an at least partially transparent casting compound. The surface of the casting compound may be flat. As a result of the combination of reflector, which is designed in the form of at least one curved side wall, and casting compound, in particular with a flat surface, the outcoupling of light from the cavity can be further improved and optimized or maximized.

The side wall may in particular comprise an at least approximately parabolic profile as seen from the bottom of the cavity to the housing underside. In this way, a geometric shape can be implemented in which the side wall contributes particularly well to improving the beam shaping.

The curved profile of the side wall may in particular be designed such that the side wall projects further into the cavity in the region of the bottom than in the region of the underside of the housing.

According to a preferred embodiment, which is also claimed herein by means of an independent claim, at least one of the cavities, preferably the second cavity with the light detector, is filled with an absorbing material, in particular an absorbing casting compound, from the bottom to a specified height, and the cavity is filled with a transparent material, in particular a transparent casting compound, from the specified height to the height of the underside of the housing. Light impinging on the absorbing casting compound is thus absorbed by the casting compound and therefore can no longer pass to the detector, e.g., by means of multiple reflections, and be detected there. The quality or the signal-to-noise ratio of the signal detected by the detector can thereby be improved.

The light detector is preferably arranged on the bottom of the second cavity, wherein the surface of the light detector on which a light-sensitive region of the light detector is located faces the underside of the housing, and wherein the specified height corresponds at least substantially to the distance that the surface of the light detector with the light-sensitive region has to the bottom of the second cavity. Light that does not directly pass onto the light-sensitive region but reaches the region with the absorbing casting compound in addition to the detector can thus be absorbed.

On the underside of the housing, in an edge region surrounding the first cavity, the color of the edge region may correspond to the color of the side wall or of the bottom of the first cavity. The reflectivity of the edge region can thereby be improved.

An at least partially transparent cover may be arranged on the underside of the housing. The cover is in particular transparent to the light emitted by the light emitter.

An integrated circuit may be arranged on the upper side of the housing, in particular above the second cavity for the light detector. The integrated circuit may in particular be arranged in a cavity that is open toward the upper side of the housing. This cavity may likewise be closed or closable by means of a cover.

The at least one light emitter is preferably a light-emitting diode or a light-emitting diode chip. The light emitter preferably enables an energy-efficient emission of light having at least one wavelength from a defined spectral range.

The light detector may be a photodetector. The light detector can enable a reliable and cost-effective detection of the light emitted by the light emitter.

Embodiments also relate to a portable electronic device, in particular an activity or fitness tracker or a smart watch, comprising a sensor device according to embodiments of the invention and a fastening device, in particular a wristband, connected to the sensor device, in particular its housing, for fastening the sensor device to a body part of a person, in particular such that the underside of the sensor device faces the body part, such as an arm, and/or rests against the body part.

BRIEF DESCRIPTION OF THE DRAWINGS

The invention is explained in more detail below with reference to the exemplary embodiments. In the figures:

FIG. 5A shows a plan view of a sensor device according to a sixth exemplary embodiment;

FIG. 5B-1 shows a perspective view of the sensor device of FIG. 5A cut along cutting line B-B;

FIG. 5B-2 shows another perspective view of the sensor device of FIG. 5A cut along cutting line B-B;

FIG. 5C shows a perspective view of the sensor device of FIG. 5A cut along cutting line A-A;

FIG. 5D shows a perspective view of a modification of the sensor device of FIG. 5A cut along cutting line A-A;

DETAILED DESCRIPTION OF ILLUSTRATIVE EMBODIMENTS

Figure 1:
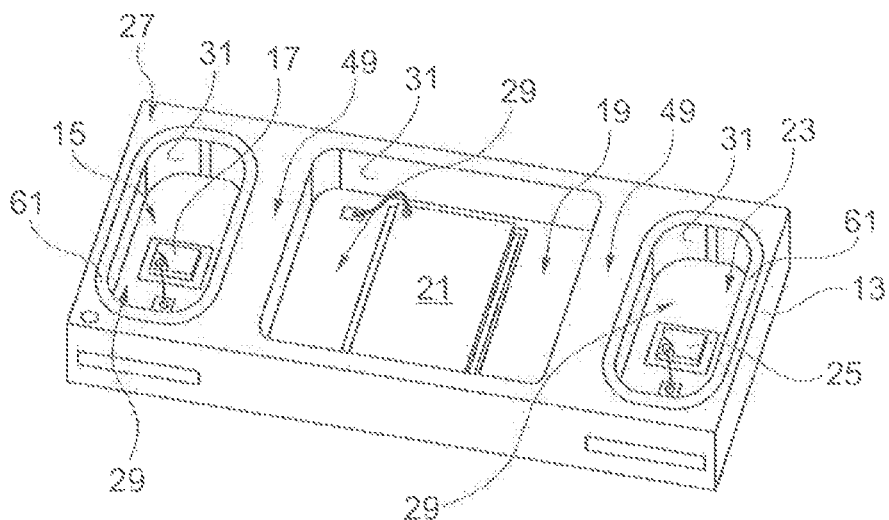
FIG. 1 shows a perspective view of a sensor device according to a first exemplary embodiment.

The sensor device shown in FIG. 1 is provided in particular for measuring at least one vital parameter of the human body. A first cavity 15 in which a first light emitter 17 is arranged is formed in a housing 13 of the sensor device. The housing 13 also comprises a second cavity 19 in which a first light detector 21 is arranged. The housing 13 comprises a third cavity 23 in which a second light emitter 25 is arranged. As FIG. 1 shows, the second cavity 19 with the first light detector 21 is arranged between the two cavities 15, 23 with the light emitters 17, 25. The cavities 15, 19, 23 are separated from one another by a respective partition wall 49.

Each of the cavities 15, 19, and 23 comprises an opening on the underside 27 of the housing 13. Each of the cavities 15, 19, and 23 is thus open toward the underside 27 of the housing 13. As a result, light can pass from the respective cavity 15, 19, 23 to the outside or into the respective cavity. The light emitted by the light emitters 17, 25 can in particular pass from the respective cavity 15, 23 to the outside, and light can pass into the second cavity 19 and to the first light detector 21 where it can be detected.

Each of the cavities 15, 19, and 23 comprises a bottom 29 and a peripheral side wall 31 extending between the respective bottom 29 and the underside 27 of the housing 13. In the sensor device of FIG. 1, the bottom 29 and the side wall 31 of the cavities 15, 23 with the light emitters is designed differently in terms of color than the bottom 29 and the side wall 31 of the cavity 19 with the light detector 21.

The bottom 29 and the side wall 31 of the first cavity 15 and of the third cavity 23 are in particular white, whereas the bottom 29 and the side wall 31 of the second cavity 19 are black. The white color may be implemented in that the bottom 29 and the side wall 31 of the first and the third cavity 15, 23 are provided with a white layer, whereas the bottom 29 and the side wall 31 of the second cavity 19 are already black on account of the black housing 13. As a result of the color of the first and the third cavity 15, 23, the latter have a higher reflectivity than the second cavity 19 with the first light detector 21. As a result of the white cavities 15, 23, multiple reflections of the light emitted by the light emitters 17, 25 can in particular take place at the bottom 29 or at the side wall 31 of the respective cavity, whereby better outcoupling of the emitted light from the respective cavity 15, 23 can be achieved. As a result of the absorbing properties of the black side wall 31 and of the black bottom 29 of the second cavity 19, an improved absorption of light also takes place, which enters the detector cavity 19 and does not impinge directly on the detector 21.

Optionally, at least some of the cavities 15, 19, and 23 may be filled with a preferably transparent casting compound, e.g., made of a resin or a silicone. The respective casting compound may comprise a flat surface.

Reflections, such as total reflections, may occur in the emitter cavities 15, 23 at the interface between the casting compound and the surroundings. In this case, the reflected light cannot exit the respective cavity 15, 23. However, the number of multiple reflections in the cavities 15, 23 with the white, reflecting surfaces can be significantly increased in comparison to a black cavity. A significant number of multiple reflections can in particular be achieved. An initially reflected light beam can therefore circulate in the respective cavity 15, 23 and be reflected multiple times at the bottom 29 or at the side wall 31 until the light beam again impinges on the interface between casting compound and surroundings, e.g., at an optimal angle, and can leave the cavity 15, 23. In particular in combination with a casting compound, the outcoupling efficiency from such a cavity 15, 23 occupied by a light emitter 17, 23 can therefore be improved by the white surfaces in the emitter cavities 15, 23.

A lens or another beam-shaping element may be arranged or formed on the surface of a respective casting compound (not shown).

The bottom 29 and the side wall 31 of the first and the third cavity 15, 23 need not necessarily be white to achieve improved reflectivity, which may be implemented, for example, by applying a layer of titanium dioxide ($TiO_2$) to said surfaces. As a further example, said surfaces may also be gold, e.g., by means of an applied gold layer. As a further example, silver is mentioned, which may be implemented, for example, by applying a silver or aluminum layer to said surfaces.

It is also not necessary for both the bottom 29 and the side wall 31 of both cavities 15, 23 to be designed differently in terms of color than the bottom 29 and the side wall 31 of the second cavity 19. Such a color difference may also be implemented only in one of the emitter cavities 15, 23. It is also possible for only a portion of the surface formed by the respective bottom 29 or the respective side wall 31 to be designed differently in terms of color than the corresponding surface of the detector cavity 19.

Optionally, an edge region 61 on the underside 27 of the housing 13 which encloses the first cavity 15 or the third cavity 23 may have the same color as the bottom 29 and/or the side wall 31 of the respective cavity.

Figure 2:
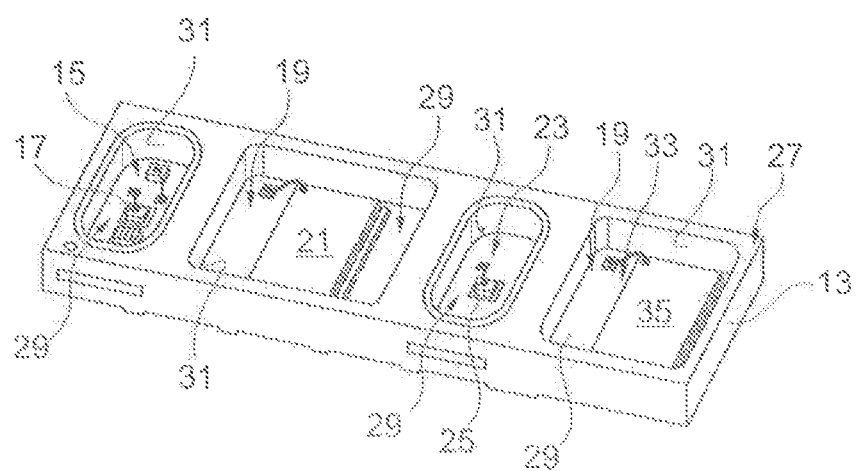
FIG. 2 shows a perspective view of a sensor device according to a second exemplary embodiment.

The sensor device shown in FIG. 2 differs from the sensor device of FIG. 1 substantially in that the sensor device of FIG. 2 comprises a further, fourth cavity 33, on the bottom 29 of which a further, second light detector 35 is arranged. The bottom 29 and the side wall 31 of the fourth cavity 33 are black in the example shown, in accordance with the design of the second cavity 19 and in order to achieve improved absorption in the detector cavities 19, 33.

In the device of FIG. 2, as in the device of FIG. 1 and the further described devices, an optional, in particular transparent, casting compound, which preferably forms a flat surface, may be provided in one or more of the cavities 15, 19, 23, 33. The casting compound may contribute, in particular in combination with the white surfaces of the respective cavity 15, 23, to improving the beam shaping and outcoupling efficiency from the respective cavity 15, 23 with the light emitters 17, 25.

Figure 3:
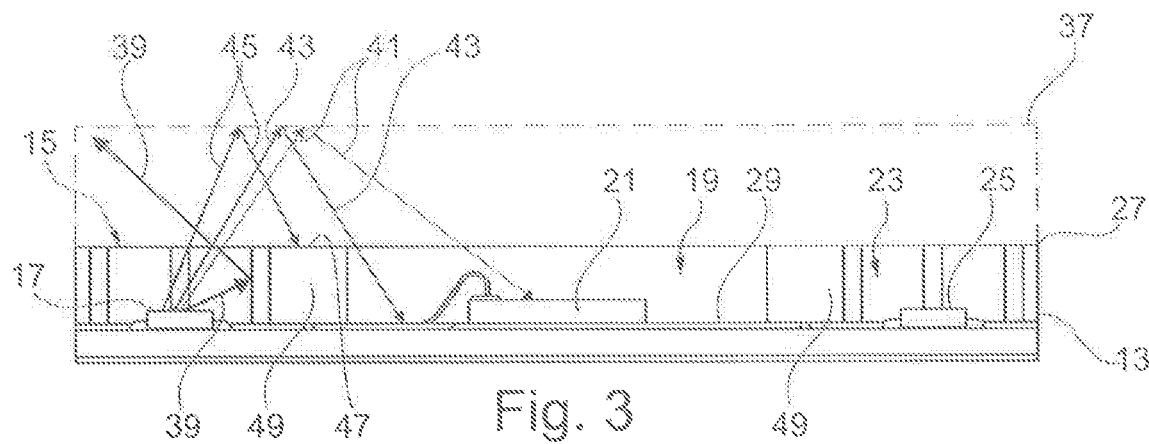
FIG. 3 shows a sectional side view of a sensor device according to a third exemplary embodiment.

The sensor device of FIG. 3 structurally corresponds to the sensor device of FIG. 1. A cover 37 is arranged on the underside 27 of the housing 13 and is transparent to the light emitted by the light emitters 17, 25. FIG. 3 shows some possible light beams by way of example for illustrative purposes. As can be seen, the light beam 39 emitted by the light emitter 17 is reflected at the side wall 31 of the first cavity 15. Due to the improved reflectivity of the side wall 31 of the first cavity 15, improved outcoupling from the first cavity 15 is achieved for such light beams impinging on the side wall 31 or the bottom 29 of the first cavity 15.

When a casting compound, in particular a flat casting compound, is used in a cavity 15, 23 with a light emitter 17, 25, reflections, such as total reflections, occur at the interface between the casting compound and the surroundings. A portion of the light emitted by the respective light emitter 17, 25 thus does not pass to the outside but remains in the cavity 15, 23. Since the side wall 31 and the bottom 29 of the respective cavity 15, 23 are white, this light, in comparison to a cavity with absorbing, black walls, can be reflected multiple times by the bottom 29 or the side wall 31 of the cavity until it can ideally exit the cavity into the surroundings. Precisely in combination with a flat casting compound, highly reflective surfaces, e.g., white surfaces, in an emitter cavity thus contribute to an improvement in the outcoupling efficiency, in particular in comparison to a black cavity.

As FIG. 3 also illustrates, light beams are reflected at the cover 37. In this case, as illustrated by the light beam 41 by way of example, light beams may be reflected at the cover 37 in such a way that they pass directly to the light detector 21 and can thus be detected by it. Other reflected light beams, such as the drawn-in light beams 43 and 45, do not pass directly to the light detector 21 after the reflection at the cover 37. Like the light beam 43, light beams may reach, for example, the bottom 29 of the second cavity 19 or, like the light beam 45, may impinge on a surface 47 of the partition wall 49 located on the underside 27 of the housing 13. Since both the surface 47 and the bottom 29 of the second capacity 19 are black, these light beams can be absorbed. Reflection of these beams thus does not take place. Such beams can therefore be effectively prevented from passing to the light detector 21, for example by multiple reflections at surfaces of the housing 13 or of the cover 37, and falsifying the detector signal there. Reflections at the surface of an optional casting compound, which can also falsify the detector signal, can also be avoided or at least reduced by the absorbing surfaces. An improvement in the signal-to-noise ratio of the detected signal can thus be achieved by the absorbing surfaces.

Figure 4A:
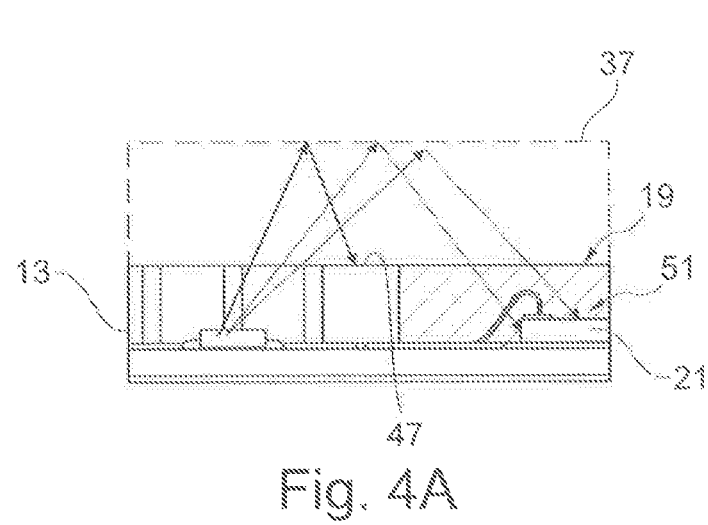
FIG. 4A shows a sectional side partial view of a sensor device according to a fourth exemplary embodiment.

In the sensor device of FIG. 4A shown in a detailed view, a transparent casting compound 51, which completely fills the second cavity 19, is introduced into the second cavity 19.

Figure 4B:
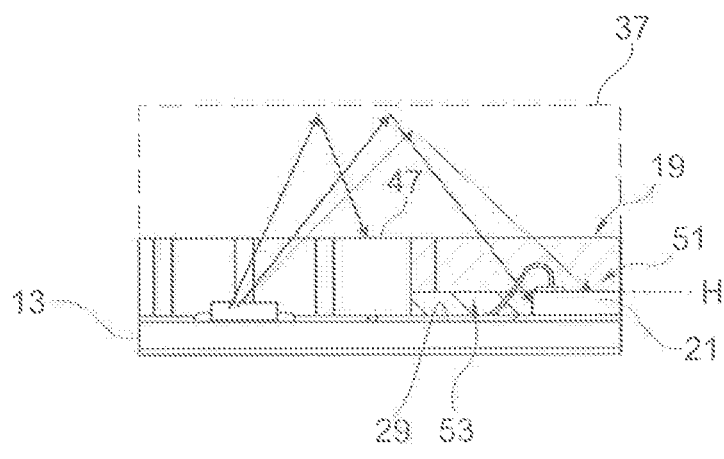
FIG. 4B shows a sectional side partial view of a sensor device according to a fifth exemplary embodiment.

In contrast to the sensor device of FIG. 4A, the second cavity 19 in the sensor device of FIG. 4B is filled from the bottom 29 to a specified height H with an absorbing casting compound 53. From the specified height H to the height of the underside 27 of the housing 13, the second cavity 19 is filled with transparent casting compound 51. The terms "transparent" and "absorbing" relate in particular to the light emitted by the light emitters 17, 25. Incident light can be absorbed by the absorbing casting compound 53 so that it can no longer, for example after further multiple reflections, be detected by the detector 21.

The structure of the sensor device of FIG. 5A corresponds at least substantially to the structure of the sensor device of FIG. 2. As can be seen from the illustrations of FIGS. 5B-1 and 5B-2, all cavities 15, 19, 23, 33 may be designed with straight side walls 31. In particular, the side walls 31 of the first cavity 15 and of the third cavity 23, which are provided with a respective light emitter 17, 25, are straight. Said side walls 31 extend orthogonally from the bottom 29 of the respective cavity 15, 23 to the underside 27 of the housing 13. This profile may be implemented along the entire peripheral direction U of the side walls 31, as can also be seen from the illustration of FIG. 5C.

As FIG. 5B-2 shows, all cavities 15, 19, 23, and 33 may be filled with a transparent casting compound 51. The combination of a transparent and an absorbing casting compound, as described with reference to FIG. 4B, may also be implemented. According to FIG. 5B-2, each casting compound 51 forms a planar surface. Other surface shapes, e.g., lens-like surfaces, are also possible here.

As FIG. 5A illustrates, more than one light emitter may also be provided in a cavity, cf. the left cavity 15. For example, in addition to the first light emitter 17, two further light emitters 63, 65 are arranged on the bottom 29 of the cavity 15 of FIG. 5A. The light emitters 17, 63, and 65 may be designed to emit light at different wavelengths. One of the detectors 21, 35 may have a color filter in order to, for example, be able to detect only the light originating from one of the light emitters 17, 63, and 65.

At least one side wall 31, preferably of the first or the third cavity 15, 23, as FIG. 5D shows, may comprise a curved profile at least over a section of the side wall 31 extending in the peripheral direction U, as seen from the bottom 29 of the respective cavity 15, 23 to the underside 27 of the housing 13. Due to its geometry, the curved section of the side wall 29 can serve as a reflector for the light emitted by the light emitters 17, 25. The outcoupling efficiency from the cavities with emitters can thereby be further improved.

As seen in the peripheral direction U of a respective side wall 31, a section of the side wall 31 may also extend at least substantially orthogonally from the bottom 29 to the housing underside 27, whereas another section comprises a curved profile from the bottom 29 to the underside 27. The side wall 31 of a cavity may thus be straight or curved in sections. The curved profile here preferably extends approximately parabolically, as FIG. 5D shows.

Figure 6A:
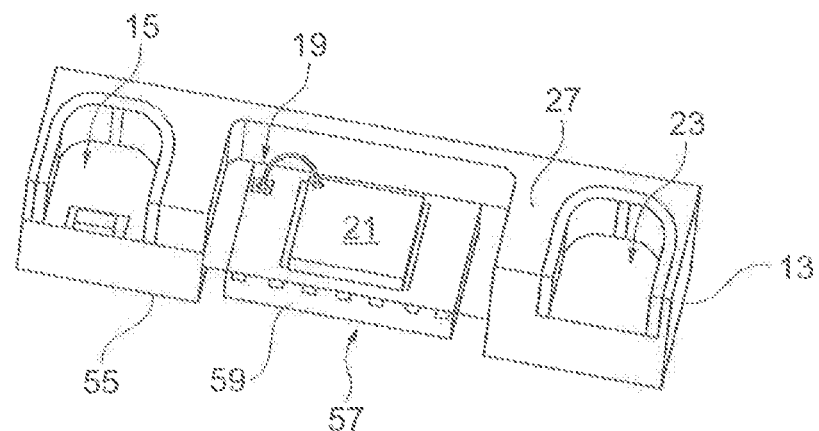
FIG. 6A shows a perspective sectional view of a sensor device according to a seventh exemplary embodiment.

On the upper side 55 of its housing 13, the sensor device of FIG. 6A comprises a further, fifth cavity 57 which is open toward the upper side 55. However, the fifth cavity 57 may also be closed toward the upper side 55, e.g., by a cover on the upper side 55. Preferably, the fifth cavity 57 is located above the second cavity 19 with the light detector 21, and an integrated circuit 59 is arranged in the fifth cavity 57. The circuit 59 may be connected to and control the light emitters 17, 25 as well as the light detector 21.

The circuit 59 may be designed, for example, for evaluating the detected signal, e.g., in order to determine the heart rate.

Figure 6B:
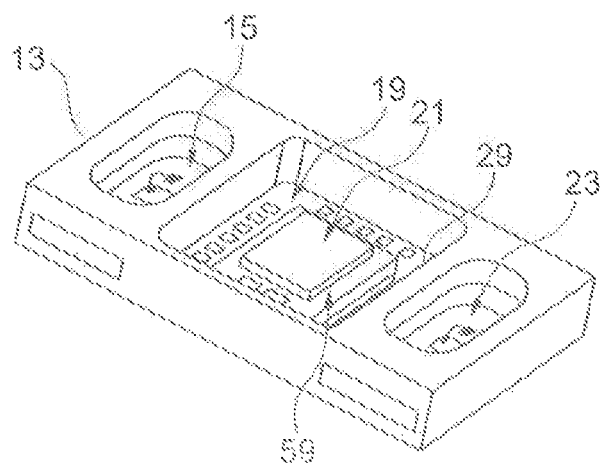
FIG. 6B shows a perspective view of a sensor device according to an eighth exemplary embodiment.

In the sensor device of FIG. 6B, the integrated circuit 57 is located at the bottom 29 of the second cavity 19, and the first light detector 21 is arranged on the integrated circuit 59.

Each of the sensor devices described may be part of a portable electronic device, such as an activity or fitness tracker or a smart watch. The housing of the sensor device may correspond to the housing of the device or be integrated therein. The housing may be connected to a wristband in order to attach the device to a body part of a test person, in particular in such a way that the underside of the sensor device or the cover arranged thereon rests against the body part. The sensor device may, for example, be used as a heart rate sensor.

The invention claimed is:
1. A sensor device comprising:
a housing having at least a first cavity and a second cavity;
at least one light emitter arranged in the first cavity; and
at least one light detector arranged in the second cavity,
wherein each of the cavities comprises an opening at an underside of the housing so that light from the respective cavity is passable to an outside or from the outside into the respective cavity,
wherein each of the cavities comprises a bottom opposite the underside of the housing and a peripheral side wall extending between the bottom and the underside of the housing,
wherein at least one of the cavities is filled with an absorbing material from the bottom to a specified height, and with a transparent material from the specified height to a height of the underside of the housing,
wherein the at least one light detector is arranged on the bottom of the second cavity,
wherein a surface of the at least one light detector on which a light-sensitive region of the at least one light detector is located faces the underside of the housing, and wherein the specified height corresponds to a distance from the surface of the light-sensitive region of the at least one light detector to the bottom of the second cavity.

2. The sensor device according to claim 1, wherein the bottom or the side wall of the first cavity is designed differently in terms of color than the bottom or the side wall of the second cavity.

3. The sensor device according to claim 2, wherein the first cavity has a higher reflectivity than the second cavity.

4. The sensor device according to claim 2, wherein the second cavity has a higher absorptance than the first cavity.

5. The sensor device according to claim 1, wherein the bottom or the side wall of the first cavity are at least white, or wherein the bottom or the side wall of the first cavity comprise a metallic layer.

6. The sensor device according to claim 1, wherein the bottom or the side wall of the second cavity are at least black.

7. The sensor device according to claim 1, wherein at least one of the cavities is filled with a transparent material, and wherein the transparent material comprises a flat surface.

8. The sensor device according to claim 1, further comprising a partition wall located between the first cavity and the second cavity, wherein a surface of the partition wall is located on the underside of the housing and has a high absorptance.

9. The sensor device according to claim 8, wherein the partition wall has the same absorptance as the bottom or the side wall of the second cavity.

10. The sensor device according to claim 8, wherein the surface of the partition wall is at least black.

11. The sensor device according to claim 1, wherein the side wall of at least one of the cavities extends at least orthogonally from the bottom of the cavity to the underside of the housing.

12. The sensor device according to claim 1, wherein the side wall of at least one of the cavities comprises a curved profile from the bottom of the cavity to the underside of the housing at least over a section of the side wall extending in a peripheral direction.

13. The sensor device according to claim 12, wherein the curved profile of the side wall is designed such that the side wall projects further into the cavity in a region of the bottom than in a region of the underside of the housing.

14. The sensor device according to claim 1, further comprising an at least partially transparent cover, wherein the cover is arranged on the underside of the housing, and wherein the cover is configured to be transparent for light of the light emitter.

15. The sensor device according to claim 1, further comprising an integrated circuit arranged on an upper side of the housing, wherein the integrated circuit is arranged in a further cavity that is open on the upper side, and wherein the upper side is located opposite to the underside.

16. The sensor device according to claim 1, wherein the sensor device is configured to measure at least one vital parameter of a human body.

17. The sensor device according to claim 1, wherein the second cavity with the at least one light detector is filled with an absorbing casting compound from the bottom to the specified height, and with a transparent casting compound from the specified height to the height of the underside of the housing.

18. A portable electronic device comprising:
the sensor device according to claim 1; and
a fastening device connected to the sensor device, the fastening device being configured to fasten the sensor device to a body part of a person.

19. The portable electronic device according to claim 18, wherein the portable electronic device is an activity tracker or smart watch, wherein the fastening device is a wristband, and wherein the underside of the housing faces the body part or rests against the body part.

* * * * *